United States Patent
Klang et al.

(10) Patent No.: US 7,722,522 B2
(45) Date of Patent: May 25, 2010

(54) BRACE PROVIDING FOCUSED ENERGY FOR MEDICAL THERAPY

(76) Inventors: Gregg Alan Klang, 31891 Via Oso, Coto De Caza, CA (US) 92679; Lars Ankor, 1310 East Ocean, #1702, Long Beach, CA (US) 90802; Daniel Klang, 5 Regato, Rancho Santa Margarita, CA (US) 92688

( * ) Notice: Subject to any disclaimer, the term of this patent is extended or adjusted under 35 U.S.C. 154(b) by 41 days.

(21) Appl. No.: 12/069,801

(22) Filed: Feb. 11, 2008

(65) Prior Publication Data
US 2009/0203955 A1 Aug. 13, 2009

(51) Int. Cl.
*A61N 1/00* (2006.01)

(52) U.S. Cl. ......................................... 600/15

(58) Field of Classification Search ................ 600/9–15
See application file for complete search history.

(56) References Cited

U.S. PATENT DOCUMENTS

| | | | |
|---|---|---|---|
| 4,456,001 A | 6/1984 | Pescatore | |
| 4,501,265 A | 2/1985 | Pescatore | |
| 4,548,208 A | 10/1985 | Niemi | |
| 4,616,629 A | 10/1986 | Moore | |
| 4,635,643 A | 1/1987 | Brown | |
| 4,662,378 A | 5/1987 | Thomis | |
| 4,757,804 A * | 7/1988 | Griffith et al. ................ | 600/13 |
| 4,932,951 A | 6/1990 | Liboff et al. | |
| 4,974,114 A | 11/1990 | Kammerer | |
| 5,088,976 A | 2/1992 | Liboff et al. | |
| 5,139,474 A * | 8/1992 | Lamond et al. ............... | 600/15 |
| 5,181,902 A * | 1/1993 | Erickson et al. ............... | 600/13 |
| 5,195,941 A | 3/1993 | Erickson et al. | |
| 5,401,233 A | 3/1995 | Erickson et al. | |
| 5,478,303 A | 12/1995 | Foley-Nolan et al. | |
| 5,518,496 A | 5/1996 | McLeod et al. | |
| 5,743,844 A | 4/1998 | Tepper et al. | |
| 5,782,743 A | 7/1998 | Russell | |
| 5,993,375 A | 11/1999 | Engel | |
| 5,997,464 A | 12/1999 | Blackwell | |
| 6,024,691 A | 2/2000 | Tepper et al. | |
| 6,139,486 A | 10/2000 | Matuszewski et al. | |
| 6,146,324 A | 11/2000 | Engel | |
| 6,174,276 B1 | 1/2001 | Blackwell | |
| 6,701,185 B2 | 3/2004 | Burnett et al. | |
| 6,776,753 B1 | 8/2004 | Holcomb | |
| 7,175,587 B2 | 2/2007 | Gordon et al. | |
| 2004/0210254 A1 | 10/2004 | Burnett et al. | |
| 2005/0080315 A1 | 4/2005 | Holcomb | |
| 2005/0101828 A1 | 5/2005 | Butler et al. | |

* cited by examiner

*Primary Examiner*—John P Lacyk
(74) *Attorney, Agent, or Firm*—Gene Scott; Patent Law & Venture Group

(57) ABSTRACT

An electromagnetic body-treatment device includes a brace of an electromagnetically transparent material which is shaped for removable conforming application to a contour of the human body. One or more multi-turn electrical coils are embedded in the brace and are oriented to establish a magnetic flux density in a therapy site about which the brace is mounted. A plurality of receivers are positioned in the brace in relative opposition to the coils. Permeable material slugs are pressed into the receivers to control the form factor of the flux density. A pulse signal generator drives the coil with low-voltage unidirectional pulses which are propagated as an associated succession of bursts in the magnetic flux density which is focused by the slugs on the therapy site.

15 Claims, 2 Drawing Sheets

BRACE PROVIDING FOCUSED ENERGY FOR MEDICAL THERAPY

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

REFERENCE TO A "MICROFICHE APPENDIX"

Not applicable.

SEQUENCE LISTING

Not applicable.

BACKGROUND OF THE INVENTION

1. Field of the Present Disclosure

This disclosure relates generally to energetic medical stimulation for therapeutic healing and especially bone growth stimulation, and more particularly to devices for producing and directing such stimulation to targeted therapy sites.

2. Description of Related Art Including Information Disclosed Under 37 CFR 1.97 and 1.98

The following patents have been found to particularly relate to aspects of the presently described and illustrated invention for which patent protection is sought.

Pescatore, U.S. Pat. No. 4,456,001, discloses a boot removably adapted for attachment to an equine hoof and carrying at least one multi-turn electrical coil which effectively surrounds at least the bottom of the hoof. A pulse generator and power source are self-contained in a housing carried at the back side of the boot, with provision for electrically exciting the coil with a succession of therapeutically beneficial low-voltage unidirectional asymmetrical pulses.

Niemi, U.S. Pat. No. 4,548,208, discloses an apparatus for treating a patient which induces an electric current in the body through external application of an electromagnetic field. The apparatus includes means for controlling the magnitude of the induced electric current by sensing the electromagnetic field and automatically controlling its strength. The sensing may be accomplished through time multiplexed use of the field inducing coil or through the use of a separated, dedicated coil.

Moore, U.S. Pat. No. 4,616,629, discloses an invention that contemplates a single-coil configuration adapted for embedment in an orthopedic cast, for use in applying electromagnetic signals for osteogenic therapy. An otherwise flat circular multiple-turn coil is so permanently deformed as to establish a first generally U-shaped projection of the coil in a first viewing aspect which is normal to the coil axis, the deformation being further such as to establish a second generally U-shaped projection of the coil in a second viewing aspect which is normal to the coil axis, said viewing aspects being orthogonally related. The depth of the deformation is common to each of the U-shapes and is approximately one fourth of the combined span of the two U-shapes.

Liboff et al., U.S. Pat. No. 4,932,951, and U.S. Pat. No. 5,088,976, disclose apparatus and methods for regulating tissue growth in vivo. The apparatus includes a magnetic field generator and a magnetic field detector for producing a controlled, fluctuating, directionally oriented magnetic field parallel to a predetermined axis projecting through the target tissue. The field detector samples the magnetic flux density along the predetermined access and provides a signal to a microprocessor which determines the average value of the flux density. The applied magnetic field is oscillated at predetermined frequencies to maintain a pre-selected ratio of frequency to average flux density. This ratio is maintained by adjusting the frequency of the fluctuating magnetic field and/or by adjusting the intensity of the applied magnetic field as the composite magnetic flux density changes in response to changes in the local magnetic field to which the target tissue is subjected. By maintaining these precise predetermined ratios of frequency to average magnetic flux density, growth characteristics of the target tissue are controlled.

Kammerer, U.S. Pat. No. 4,974,114, discloses an energy recovery system for an electrotherapy device, particularly for bone healing, which permits the device to be small, light and portable, and to have extended battery life. Included are a drive voltage source and a ground reference potential. Driving transistors are between an inductive load and, relatively, the voltage source and ground potential, with a storage capacitor connected between the latter two. The voltage source is commonly a battery, preferably a zinc-air battery. Induction load power is applied when both transistors turn on simultaneously. For energy recovery, diodes are connected between the first terminal of the inductive load and the ground potential and between the second terminal of the inductive load and the high voltage source, such that they are reversed biased when the drive transistors are conducting. When drive power is removed from the inductive load by switching off the drive transistors, a reverse EMF is established in the inductive load. As the inductive load magnetic field collapses, a reverse voltage is developed across the inductor higher than the applied voltage by an amount sufficient to forward bias the diodes. Thus, current flows from the inductive load through the diodes to the storage capacitor. Recovery of the energy stored in the inductor continues until the energy remaining is insufficient to maintain current flow to the storage capacitor.

Foley-Nolan et al., U.S. Pat. No. 5,478,303, discloses a device for the controlled emission of electromagnetic radiation for use in medical and surgical conditions in humans and animals that comprises a substrate which can be contoured to and placed in intimate contact with an area of the body of the human or animal to be treated, an electrical circuit integral with the substrate, including at least one inductance coil, and flexible with the substrate, and a power supply connected to the circuit. The electromagnetic radiation emitted by the device may be pulsed or continuous. The device has application in the alleviation of acute and chronic pain and in modulating cellular replication.

Ryaby et al, U.S. Pat. No. 4,266,532, discloses a surgically non-invasive method of and apparatus for altering the growth, repair and maintenance behavior of living tissues and, or cells by inducing voltage and concomitant current pulses of specific time-frequency-amplitude relations therewithin.

Further prior art related to the present invention includes: McLeod et al., U.S. Pat. No. 5,518,496, Erickson et al., U.S. Pat. Nos. 5,195,941 and 5,401,233, Russell, U.S. Pat. No. 5,782,743, Engel, U.S. Pat. No. 5,993,375 and U.S. Pat. No. 6,146,324, Blackwell, U.S. Pat. Nos. 5,997,464 and 6,174, 276, Matuszewski et al., U.S. Pat. No. 6,139,486, Burnett et al., U.S. Pat. No. 6,701,185, Holcomb, U.S. Pat. No. 6,776, 753 and 2005/0080315, Gordon et al., U.S. Pat. No. 7,175, 587, Burnett et al., US 2004/0210254, and Butler et al., US 2005/0101828.

The related art described above discloses a wide range of devices and electrical circuits useful for medical treatment of human ailments using electromagnetic radiation and especially magnetic flux. These devices also teach means for mounting the devices in proximity to a target therapy site. However, the prior art fails to disclose such a device that is able to target magnetic flux to the cervical skeleton in humans and particularly to medical sites of choice wherein the sites may be easily selected and changed as desired. The present disclosure distinguishes over the prior art providing heretofore unknown advantages as described in the following summary.

BRIEF SUMMARY OF THE INVENTION

This disclosure teaches certain benefits in construction and use which give rise to the objectives described below.

A magnetic flux body-treatment device includes a brace of an electro-magnetically transparent material which is shaped for removable conforming application to a selected portion of an animal's body such as an arm, leg, torso or neck and especially to the human neck as a cervical brace. One or more multi-turn electrical coils are permanently embedded in the brace and are oriented to emit magnetic flux toward a therapy site especially a site associated with the cervical skeleton. The coils are energized to function as electromagnets to produce a selectable magnetic flux density in the space defined by the brace and especially in the neck area. In one embodiment, one or more slugs of electromagnetically permeable material such as ferrite ($\alpha$-Fe) are held by the brace in positions opposing the coils and in or near the highest flux density produced by the coils. A signal generator provides the coil with low-voltage pulses which are propagated as a succession of magnetic flux bursts producing a variable flux density and which is directed or focused by the slugs especially to the therapy site.

A primary objective inherent in the above described apparatus and method of use is to provide advantages not taught by the prior art.

Another objective is to provide a brace that may be easily placed on, and taken off, a patient.

A further objective is to provide such a brace that, once applied, is able to immobilize a targeted medical therapy site.

A further objective is to provide such a brace that incorporates within it, an electrical circuit for producing a pulsed magnetic flux density in the vicinity of a targeted medical therapy site.

A further objective is to provide such a brace that incorporates within it, a means for focusing the magnetic flux density at the medical therapy site.

A further objective is to provide such a brace that incorporates a means for selecting and easily changing the form factor of the magnetic flux density within a body part.

Other features and advantages of the present invention will become apparent from the following more detailed description, taken in conjunction with the accompanying drawings, which illustrate, by way of example, the principles of the presently described apparatus and method of its use.

BRIEF DESCRIPTION OF THE SEVERAL VIEWS OF THE DRAWING(S)

Illustrated in the accompanying drawing(s) is at least one of the best mode embodiments of the present invention In such drawing(s):

DETAILED DESCRIPTION OF THE INVENTION

The above described drawing figures illustrate the described apparatus and its method of use in at least one of its preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present apparatus and its method of use.

Figure 1:
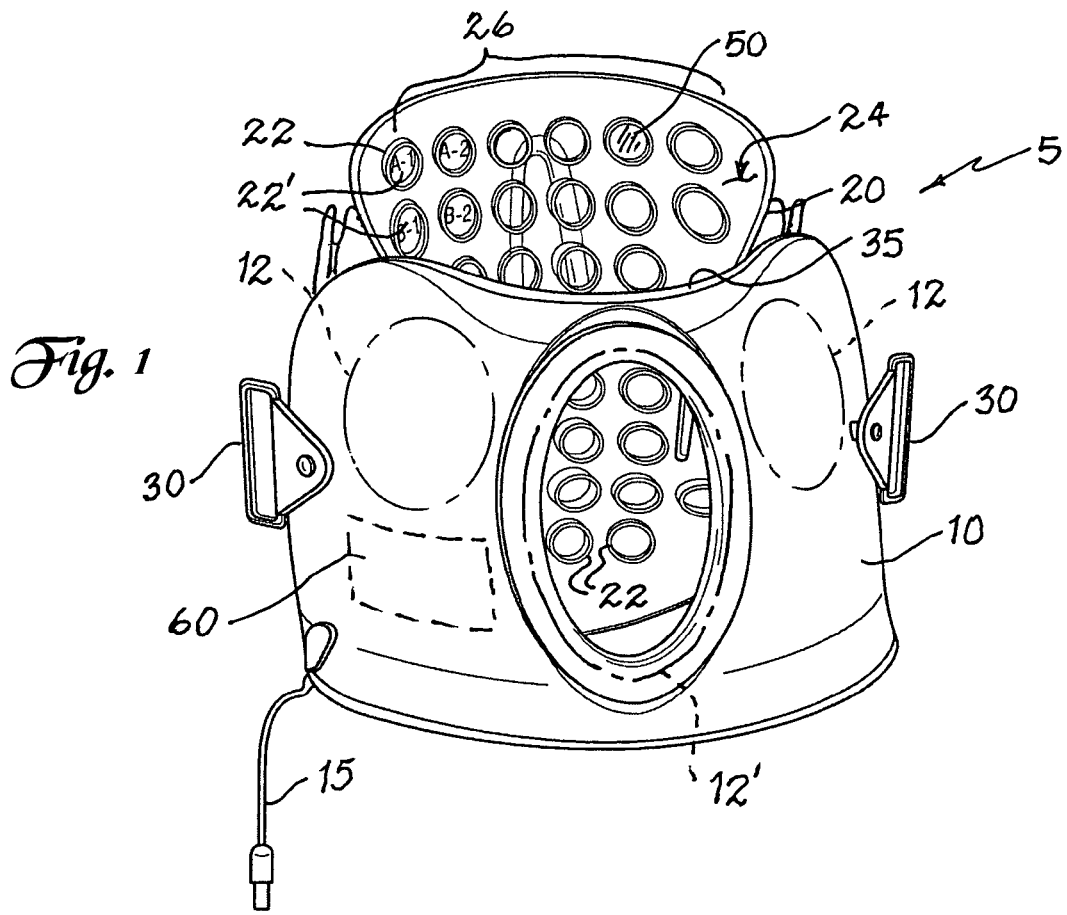
FIG. 1 is a perspective frontal elevational view of the presently described invention in an embodiment particularly suitable for therapy of the cervical skeleton.
Figure 2:
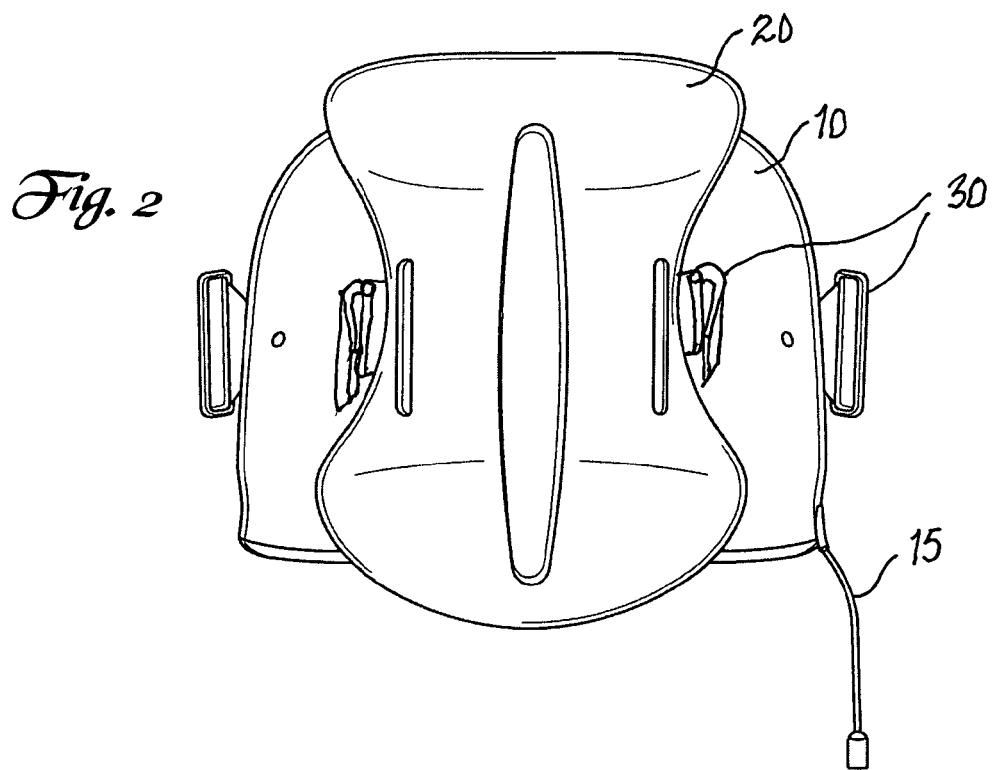
FIG. 2 is a rear view thereof.

Described now in detail is an electromagnetic medical therapy device for surgically non-invasive modification of the growth repair and maintenance behavior of living tissues and/or cells within the human body by a specific and selective change in the electrical environment at the therapy site. The present invention may be used for inhibiting growth of tissues as well. The device provides a brace 5 constructed, at least in part, of an electromagnetically transparent material such as plastic, and preferably includes a relatively flexible first portion 10 and a relatively stiff second portion 20 with the two portions peripherally joined by fasteners 30 of any type that can hold the portions 10 and 20 in secure abutment about the therapy site. The first and second portions 10, 20, are shaped for removable conforming application to a particular part of the human body, as for instance the neck, arm, leg, or other location so as to immobilize the therapy site. In the following, details are provided for use of the present invention for a cervical application wherein the brace 5 is adapted for being mounted around the neck as depicted in FIGS. 1 and 2, however, it should be kept in mind that the present invention may be applied to other parts of the human body as well in a highly similar, or identical manner as is described herein and shown in FIGS. 3 and 5. As shown in FIG. 1, one or both of the two portions 10, 20 may have a foam rubber liner 35 for comfort in clasping the invention about a body part such as the neck to immobile the neck and head while remaining relatively comfortable.

Figure 3:
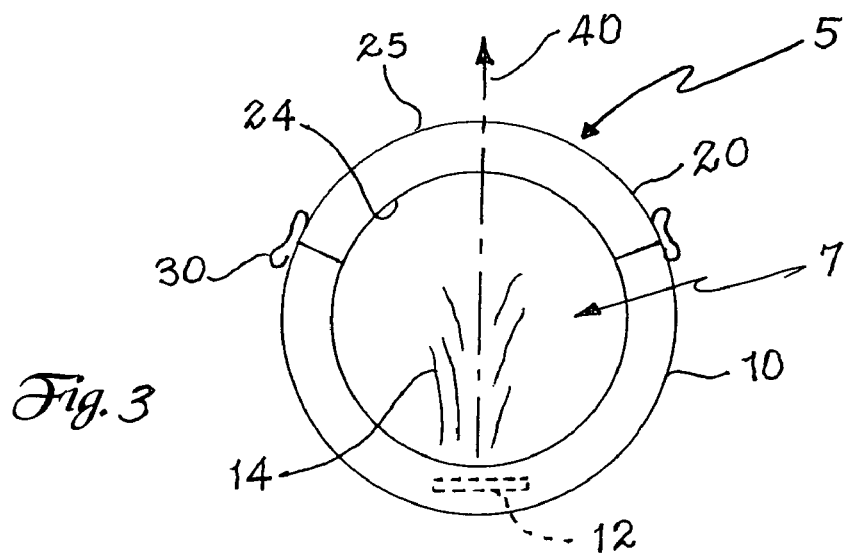
FIG. 3 is a plan view of a round brace of the presently described invention particularly useful for an arm or leg, for instance.
Figure 4:
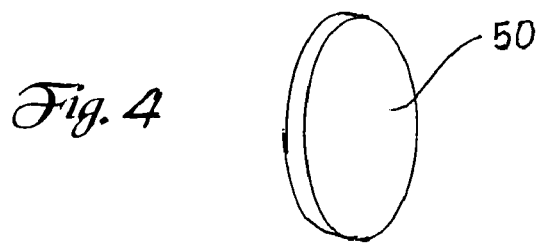
FIG. 4 is a perspective view of a ferrite slug useful for establishing a desired form-factor of a magnetic flux produced by coils within the brace.
Figure 5:
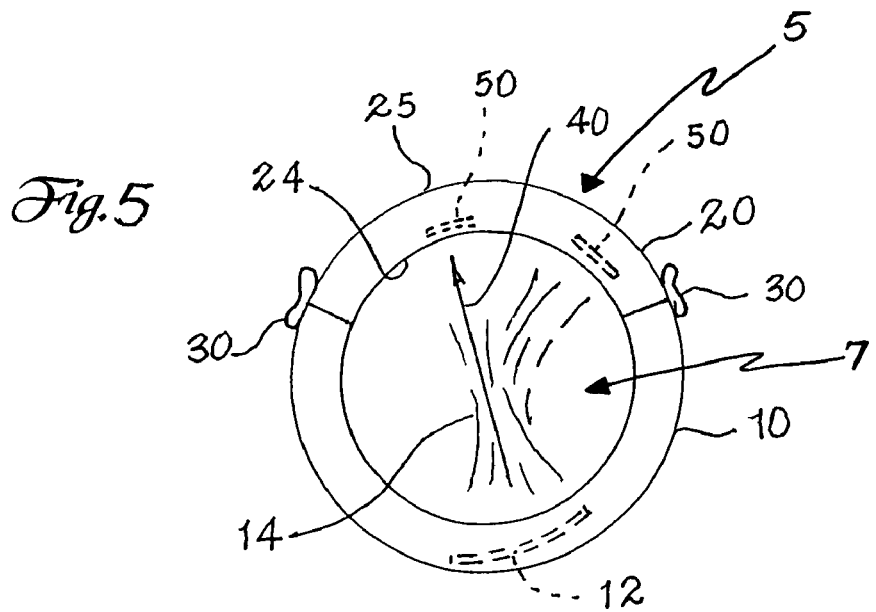
FIG. 5 is a plan view similar to FIG. 3 showing flux disbursion due to the inclusion of two of the ferrite slugs shown in FIG. 4.

A multi-turn electrical coil 12, as depicted in FIG. 1, or, alternately two or more coils 12 are preferably embedded within the first portion 10, as indicated by numerals 12 in FIG. 1, the coil 12 oriented to establish a magnetic flux density 14 in a path 40 as shown in FIGS. 3 and 5. In a further embodiment, the second portion 20 provides a plurality of receivers 22 positioned generally in opposition to the coils 12. The receivers 22 are preferably recesses formed in a surfaces 24 and or 25 of the second portion 20. The receivers 22 are preferably arranged as a matrix 26 with columns and rows, that is, in side-by-side positions over a significant portion of inside surface 24 and or outer surface 25 as shown in FIG. 1. The receivers 22 may be marked with an indicia; see element 22' in FIG. 1 such as A1, A2 ... An; B1, B2 ... Bn and so forth, so that a medical technician, or the patient can note the position of placement of a slug 50. Slugs 50 are made of a permeable material such as iron, nickel-iron alloy, or similar ferromagnetic materials including alpha ferrite, and are configured so as to be physically engaged with any one of the receivers 22, preferably by simple frictional compressive engagement by being manually pressed into the receivers 22. Alternately, receivers 22 may be pockets which can receive the slugs 50. In any case, the slugs 50 may be of any shape and any selected size and may be secured into the receivers 22 in any manner, just as long as the slugs 50 are held relatively immobile in the receivers and are able to be easily inserted and removed as desired for establishing interaction with magnetic flux 14 to form a desired path 40 as a form factor.

A signal generator 60 is in signal communication with the coil 12 (FIG. 1) to electrically excite it with a succession of low-voltage unidirectional pulses which are propagated by coil 12 as a corresponding succession of bursts in the magnetic flux density 14. According to Liboff et al., U.S. Pat. No. 4,932,951, which is hereby incorporated herein by reference, a varying flux density for stimulating bone or tissue growth, uses a pulse frequency of about 16 Hz, and a preferred magnetic flux density 14 is about $2.09 \times 10^{-5}$ Tesla. If bone or tissue growth is to be retarded, the same frequency is used with a magnetic flux density 14 of about $4.09 \times 10^{-5}$ Tesla. A preferred generator circuit is shown in Kammerer, U.S. Pat. No. 4,974,114 which employs an energy recovery system using a capacitor to receive current driven by a reverse emf established at the coil 12 between pulses as the electric field around coil 12 collapses. Kammerer is hereby incorporated herein by reference. Foley-Nolan et al, U.S. Pat. No. 5,478,303, hereby incorporated herein by reference, teaches a solid state coil circuit including copper conductor planar coils L1 and L2. Also, Ryaby et al, U.S. Pat. No. 4,266,532, hereby incorporated herein by reference, teaches an improved circuit and frequency regime of between 10 and 100 Hz with 72 Hz as an optimum. The present invention preferably employs any or all of these circuits for operating in a regime for bone growth stimulation, the alleviation of pain, inhibition of malignant tumors and other medical practice as described in the above cited references. The signal generator, coil positioning, coil size, coil type and coil configuration may be as described in the incorporated references or may be adapted from any of the prior art as would be known to one of skill in the field for each specific medical purpose.

As shown in FIG. 1, brace 5 may be a neck brace positionable around the neck of a person who will benefit, for instance, from bone growth cervical therapy as is taught in the above cited references. In this case a coil 12' is positioned within the first portion 10 frontally, adjacent to the throat area or other appropriate location, while the second portion 20 is positioned behind the neck positioning the receivers 22 adjacent to the nape of the neck. This same relative juxtaposition of the elements of the present invention applies to therapy on the limbs and other portions of the human anatomy.

Two or more coils 12 may be mounted in the first portion 10 and are preferably positioned for directing and positioning magnetic flux density 14 at the therapy site. When multiple coils 12 are used, they may obviously be connected in parallel, series-parallel, or in simple series electrical connections with the signal generator 60. It has been found preferable to use coils 12 that are identical in size, number of turns, etc., in a series circuit so that all of the coils carry equal current and therefore all of the coils 12 produce equivalent magnetic flux density 14 so that it is possible to utilize the value of flux density 14 as a constant in prescribing a method of therapy.

In a preferred embodiment, the electrical coil 12, or coils are shaped to conform with the contour of the body part that is under therapy, as shown in FIG. 5, so that the magnetic flux density 14 is directed convergently, or at least not divergently at the site of therapy for improved flux density value.

Preferably, the first portion 10 is joined to the second portion 20 by fasteners 30 positioned on opposing sides of brace 5, as shown in the figures, and are fasteners of the clasp type which are able to draw the first and second portions 10, 20 together to achieve a tight fit about the portion of the body that the brace 5 is mounted on.

Preferably, the signal generator is mounted within the brace 5, as shown in FIG. 1, and includes its own power supply such as rechargeable batteries (not shown) as is well represented in the prior art. Alternately, the signal generator is mounted within a separate case (not shown) interconnected to the coil(s) 12 within the brace 5 by wires 15. In the latter approach, the case may be carried by the user within a pocket in his or her clothing, or mounted on a belt. The latter approach is clearly depicted in Ericson et al., U.S. Pat. No. 5,401,233; see figures.

In operation, each coil 12 produces a magnetic flux density 14 which is established diametrically across the interior space 7 (FIGS. 3 and 5) circumscribed by brace 5. With brace 5 mounted around the neck, arm or leg, the magnetic flux density 14 is therefore established in the body part about which the brace 5 is secured. However, as initially stated, it is desirable to establish the magnetic flux density 14 specifically at a therapy site, i.e., a specific bone or tissue site where therapy is to be applied. When a permeable slug 50 is in place in one of the receivers, as shown in FIG. 1, the magnetic flux density 14 causes a magnetic dipole to develop in the slug 50 and this dipole causes the magnetic flux density 14 to shift selectively or focus on the slug 50. Therefore, as shown in FIG. 1, the slug 50 is placed in a receiver 22 that is closest to the desired therapy site within the body part. This has the effect of providing maximal magnetic flux density 14 and concomitant therapeutic effect at the intended site. Since it is generally impractical to move coil 12 so that its axis (path 40) is directed through the targeted therapy site, the appropriate positioning of one or more slugs 50 enables the shifting of magnetic flux density 14 toward the therapy site or focused on the therapy site. We refer to this as "flux focusing." Because the matrix of receivers 22 is spread over an appropriate area of brace 5, it is possible to place slugs 50 at locations to optimize the positioning of flux density 14 at, or very close, to a therapy site for each individual patient, that is; the form factor, i.e., configuration, of the magnetic flux density 14 within a body part is more easily and conveniently positionable.

One of the advantages of using the present invention is that the output of signal generator 60 may generally be reduced since the magnetic flux density 14 is able to be directed and focused at the therapy site Because output power may be reduced, the present invention provides an improved means for enabling portable therapy with longer battery lifetime and, or smaller batteries, a significant factor in portability and convenience of use.

The enablements described in detail above are considered novel over the prior art of record and are considered critical to the operation of at least one aspect of the apparatus and its method of use and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. An apparatus providing focussed energy for medical therapy at a therapy site in a body part, the apparatus comprising: a generally circular brace defining a circumscribed open space; an electrical coil embedded within an electro-magnetically transparent portion of the brace and oriented to establish a magnetic flux density in the open space; a pulsed signal generator in communication with the electrical coil enabling a pulse varying magnetic flux density in the open space; a slug of permeable material removably secured to the brace in a selected position wherein a form factor of the pulse varying magnetic flux density is selectively adjustable toward the therapy site.

2. The apparatus providing focussed energy for medical therapy at a therapy site in a body part of claim 1 wherein the brace is configured and enabled for rigid securement about the body part.

3. The apparatus providing focussed energy for medical therapy at a therapy site in a body part of claim 1 in which the brace is a neck brace, the coil positioned frontally centered on the laryngeal prominence, the slug positioned proximal the back of the neck.

4. The apparatus providing focussed energy for medical therapy at a therapy site in a body part of claim 1 in which the electrical coil comprises a plurality of electrical coils in electrical series-connection.

5. The apparatus providing focussed energy for medical therapy at a therapy site in a body part of claim 1 wherein the electrical coil is conformal to the body part.

6. The apparatus providing focussed energy for medical therapy at a therapy site in a body part of claim 1 wherein the brace comprises two portions joined by fasteners.

7. The apparatus providing focussed energy for medical therapy at a therapy site in a body part of claim 1 wherein the signal generator is mounted within the brace.

8. An apparatus providing focussed energy for medical therapy at a therapy site in a body part, the apparatus comprising: a generally circular brace defining a circumscribed open space; at least one electrical coil embedded within an electro-magnetically transparent portion of the brace and oriented to establish a magnetic flux density in the open space; a pulsed signal generator in communication with the at least one electrical coil enabling a pulse varying magnetic flux density in the open space; a plurality of receivers positioned in side-by-side positions forming a matrix over a significant surface of the brace; and at least one slug of permeable material removably secured within at least one of the receivers wherein a form factor of the pulse varying magnetic flux density is focused at the therapy site.

9. The apparatus providing focussed energy for medical therapy at a therapy site in a body part of claim 8 wherein the brace is configured and enabled for rigid securement about the body part.

10. The apparatus providing focussed energy for medical therapy at a therapy site in a body part of claim 8 in which the brace is a neck brace, the at least one electrical coil positioned frontally centered on the laryngeal prominence, the at least one slug positioned proximal the back of the neck.

11. The apparatus providing focussed energy for medical therapy at a therapy site in a body part of claim 8 in which the at least one electrical coil comprises a plurality of electrical coils in electrical series-connection.

12. The apparatus providing focussed energy for medical therapy at a therapy site in a body part of claim 8 wherein the at least one electrical coil is conformal to the body part.

13. The apparatus providing focussed energy for medical therapy at a therapy site in a body part of claim 8 wherein the brace comprises at least two portions joined by fasteners.

14. The apparatus providing focussed energy for medical therapy at a therapy site in a body part of claim 8 wherein the signal generator is mounted within the brace.

15. A method of focusing energy for medical therapy at a therapy site in a body part, the method comprising the steps of:
   a) rigidly and securely encircling the body part with a brace defining a circumscribed open space;
   b) embedding an electrical coil within an electro-magnetically transparent portion of the brace and orienting the electrical coil for establishing a magnetic flux density in the open space;
   c) communicating a pulsed electrical signal to the electrical coil thereby producing a pulse varying magnetic flux density in the open space; and
   d) removably securing a slug of permeable material in a receiver of the brace at a selected position for adjusting a form factor of the pulse varying magnetic flux density toward the therapy site.

* * * * *